United States Patent

Katz et al.

Patent Number: 5,891,089
Date of Patent: Apr. 6, 1999

[54] SYSTEM AND METHOD FOR CORONARY ANGIOPLASTY

[75] Inventors: Iony Katz; Abraham Licht; Teddy A. Weiss, all of Jerusalem, Israel

[73] Assignee: Hadasit Medical Research Services & Development, Jerusalem, Israel

[21] Appl. No.: 746,564

[22] Filed: Nov. 13, 1996

[30] Foreign Application Priority Data

May 15, 1995 [WO] WIPO ............................ WO95/31245

[51] Int. Cl.[6] .................................................. A61M 29/00
[52] U.S. Cl. ................. 604/97; 604/99; 606/192
[58] Field of Search ................... 604/97, 98, 99; 606/191, 192

[56] References Cited

U.S. PATENT DOCUMENTS 5,021,046  6/1991  Wallace ..................................... 604/99
5,135,488  8/1992  Foote et al. ............................... 604/97
5,273,537  12/1993  Haskvitz et al. .......................... 604/99

*Primary Examiner*—Michael Buiz
*Assistant Examiner*—Julian W. Woo
*Attorney, Agent, or Firm*—Fulbright & Jaworski, LLP

[57] ABSTRACT

There is provided a fluid pressure sensing and activating control system for coronary angioplasty, including a fluid pressure sensor and transducer connected to feed signals via an A/D converter to a processor and control unit, a pulse width generator receiving signals from the processor for activating a balloon inflator, and a fluid conduit connector attached to the output of the inflator and to the input of the fluid pressure sensor and transducer, and having a further output port connectable to an inflatable balloon. A method for dilating a section of an elastic conduit by means of an inflatable balloon inserted therein is also provided.

10 Claims, 2 Drawing Sheets

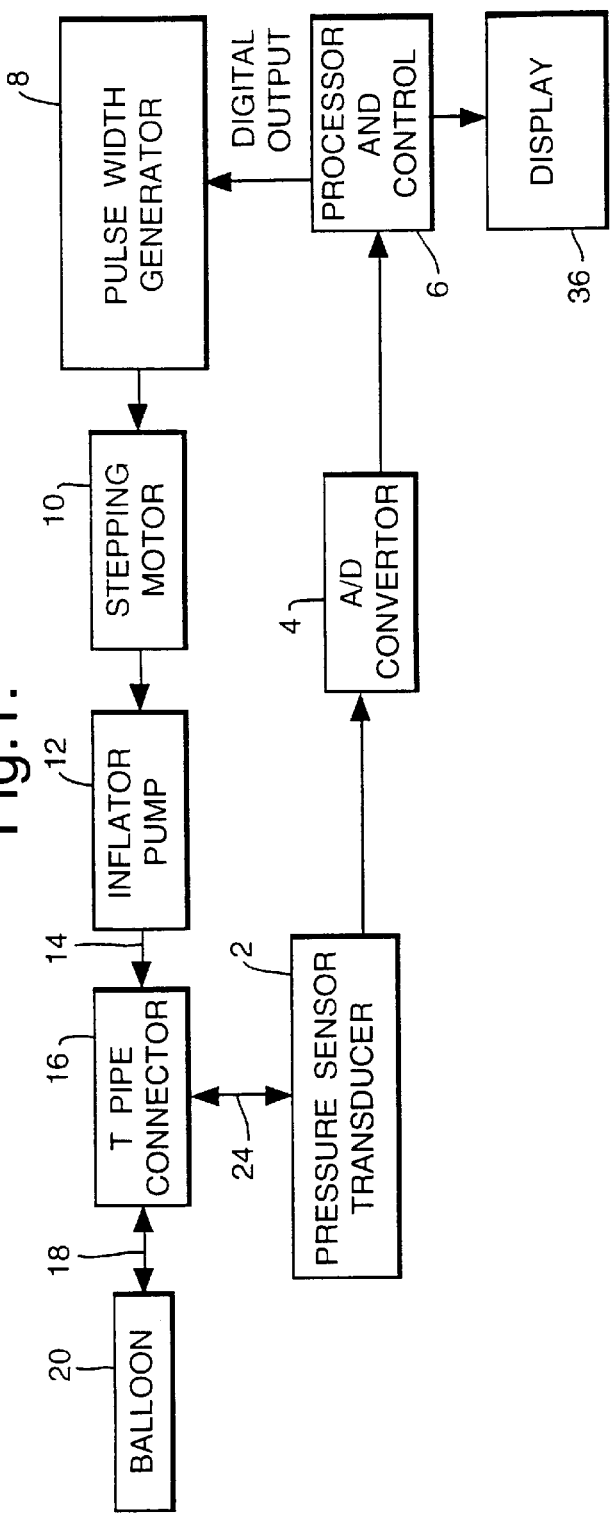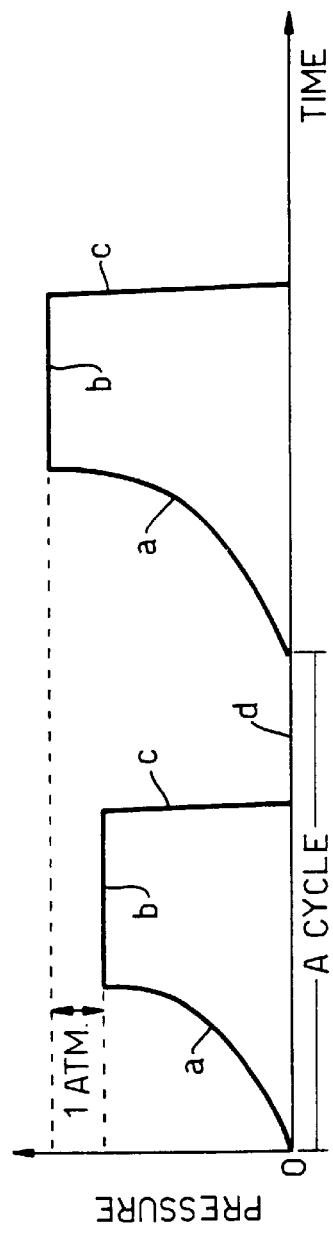

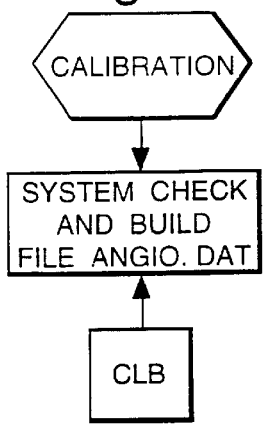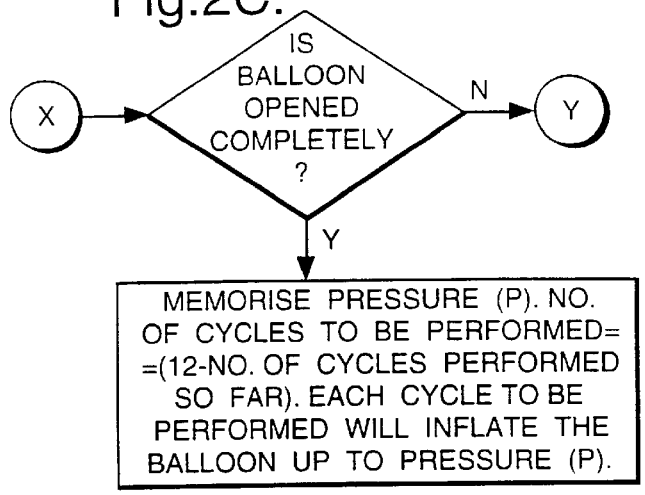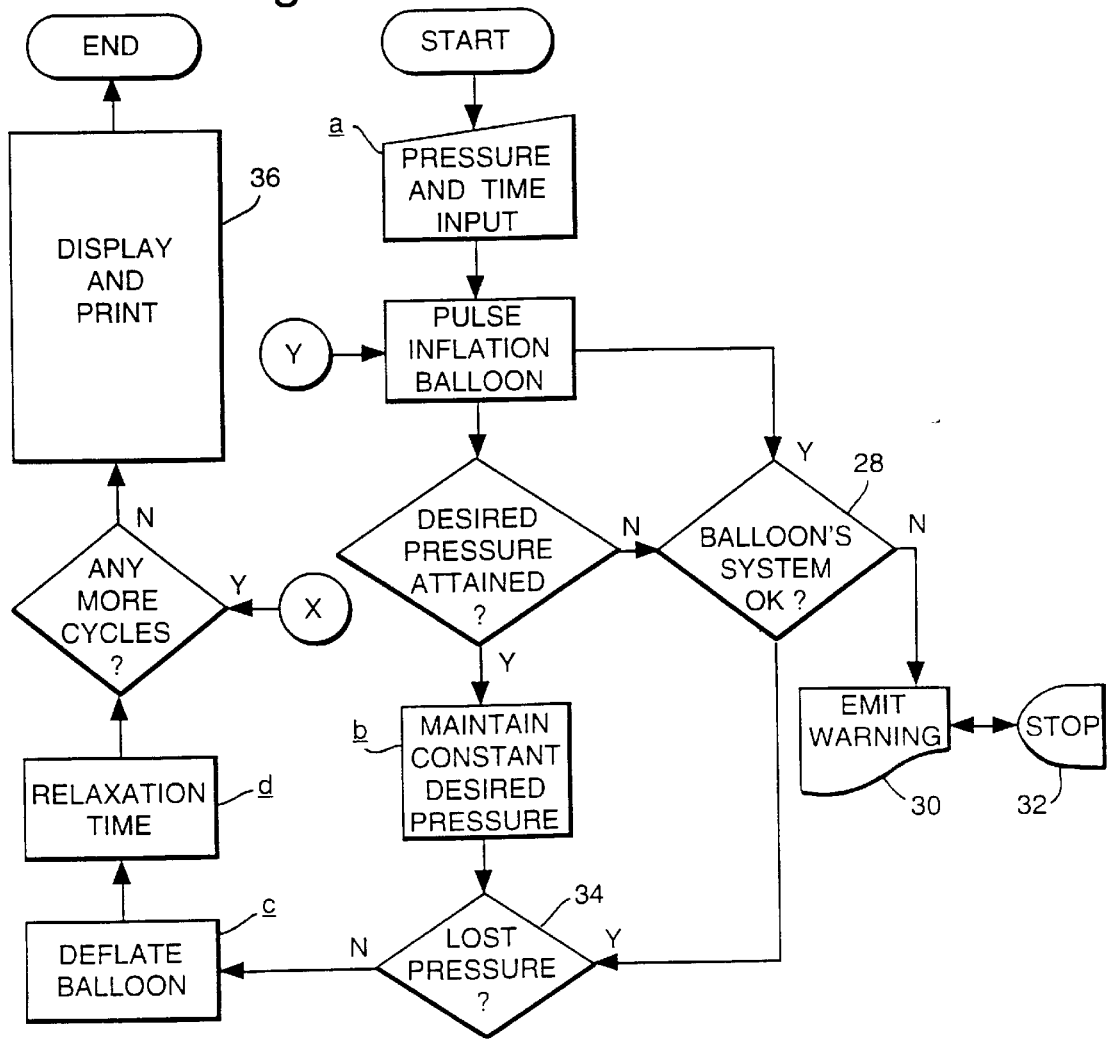

SYSTEM AND METHOD FOR CORONARY ANGIOPLASTY

RELATED APPLICATIONS

This application is related to international application PCT/US95/06382 designating the United States filed May 15, 1998.

FIELD OF THE INVENTION

The present invention relates to a fluid pressure sensing and activating control system for coronary angioplasty, hereinafter referred to as Computerized Automatic Pressure Sensor and Activation Device (CAPSAD), and to a method for dilating a section of an elastic conduit.

BACKGROUND OF THE INVENTION

Formation of plaque is the result of fat deposits and calcium compound deposits such as cholesterol and hydroxyapatite —$C_{a5}(PO_4)_3OH$— in the arterial wall, between the intima and the lumina. Whenever a serious stenosis is present, the patient complains of chest pain during stress and there is a significant risk of heart disease.

In the majority of cases, this narrowing in the coronary artery can be dilated by percutaneous angioplasty, using a manual pressure inflator. The duration of balloon inflation is, at the present time, arbitrarily defined by the operator or limited by the severity of ischemic paincaused by the inflated balloon. The early complication of this method is arterial dissection and possible occlusion, caused by the uncontrolled manual inflation of the balloon.

The injury to the arterial wall caused by the balloon may enhance growth factor secretion and induce smooth muscle cell proliferation and extra cellular matrix deposition, thus causing restenosis. The restenosis usually appears within six months after angioplasty in about 30% to 50% of the patients, thus limiting the efficacy of this procedure. Many patients will need recatheterization, repeat angioplasty and coronary bypass operations.

In most cases, the narrowed lumen is dilated by the known angioplasty method, whereby the balloon is inflated by a manual inflator pump and applies substantial mechanical pressures (e.g., 8–10 Atm.) during dilation. Since the mechanical pressure is manually increased, the pressure delivery by this method is not accurately controlled and is carried out in a relatively too short time, without any interdependence of the pressure in time. The time period of the balloon inflation is randomly determined by the performing surgeon or by the ability of the patient to endure the ischemic pains caused by the inflated balloon. In the manual method used today, the dissection of the artery is frequent, causing extensive damage to the artery, which in turn may cause acute total occlusion of the artery and may subject the patient to myocardial infarction and, on some occasions, even to restenosis.

U.S. Pat. No. 5,152,776 discloses a balloon inflation device in which the pressure monitor 70 is connected in the device between the motor 45 of the drive mechanism and the pump means 50. Both the motor 45 as operated by the drive mechanism and the pressure monitor 70 are controlled by a microprocessor unit 90. Contrary to this arrangement, according to the present invention a pressure sensor transducer is advantageously directly connected to the input of the balloon, namely, between the inflator pump and the balloon. Signals from the transducer are constantly measured and the data is conveyed to a processor and control unit. Should the pressure in the balloon suddenly rise, the control unit immediately stops the procedure. Similarly, if the pressure in the balloon drops, for example, a pressure drop caused by a leak in the balloon, rapid deflation of the balloon is effected, thus preventing further inflation and fluid leakage through the ruptured balloon.

It is therefore a broad object of the present invention to ameliorate the disadvantages of the manually operated, balloon inflator, as well as the disadvantages of the microprocessor controlled balloon inflation devices, and to provide a pressure sensing and activating control system for the performance of CAPSAD.

It is a further object of the invention to provide a, method for dilating a section of an elastic conduit by means of an inflatable balloon inserted therein, which method reduces the danger of dissection of the conduit and increases the chances of preventing collapse of the conduit after a period of time.

SUMMARY OF THE INVENTION

In accordance with the present invention, there is provided a fluid pressure sensing and activating control, system for coronary angioplasty, comprising a fluid pressure sensor and transducer connected to feed signals via an A/D converter to a processor and control unit, a pulse width generator receiving signals from said processor for activating a balloon inflation means, and a fluid conduit connector attached to the output of said inflation means and to the input of said fluid pressure sensor and transducer, and having a further output port connectable to an inflatable balloon.

The invention further provides a method for dilating a section of an elastic conduit by means of an inflatable balloon inserted therein, comprising the steps of (a) providing a system including balloon means, balloon inflating means, a pressure sensor, pressure monitoring means, and control means; (b) gradually inflating said balloon by means of fluid to a first maximal pressure, during a preset first period of time; (c) retaining said pressure inside the balloon for a preset second period of time; (d) rapidly deflating said balloon to a minimal pressure; (e) retaining said minimum pressure for a predetermined period of time, and (f) repeating steps (b) to (e), each time increasing the pressure of step (b) to a pressure higher than the previously inflated maximal pressure.

The invention will now be described in connection with certain preferred embodiments, with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

In the drawings:

FIG. 1 is a block diagram of the pressure sensing and activating control system according to the present invention;

FIGS. 2A, 2B and 2C are flow diagrams of the operation of the system of FIG. 1, and FIG. 3 is a characteristic curve of balloon inflation and deflation cycles.

DETAILED DESCRIPTION

There is seen in FIG. 1 a block diagram of the fluid pressure sensing and activating control system, including a fluid sensor and transducer 2 feeding signals via an A/D converter 4 to a processor and control unit 6. The output of the processor and control unit 6 is connected to a pulse with generator 8 controlling a stepping motor 10 operating tier inflating pump 12. The pump 12 directs fluid through a suitable tube 14 to a T-pipe connector 16, to which connector is attachable a tube 18 leading to a balloon 20. A fluid tube 24 connects the T-pipe connector 16 and the input of the pressure sensor and transducer 2.

The operation of the system will now be described, with reference also to FIGS. 2A, 2B, 2C and 3.

The first optional stage of the operation calls for the calibration of the system (FIG. 2A), wherein a balloon of the type to be used, or a similar one, is inflated at atmospheric pressure and the data obtained concerning the pressure required in overcoming the balloon's elasticity is stored. Thereupon, the balloon is replaced and after being inserted at the proper location in the artery, the balloon is first exponentially, gradually inflated by the pump 12 to a preset atmospheric pressure, as depicted by curve a of FIG. 3.

When the balloon is gradually inflated, the characteristic independence of pressure vs. volume of the balloon generates an exponential curve for pressures greater than 3 Atm., and a linear curve for pressures under 3 Atm. In this manner, the balloon's volume expands gradually at relatively small pressures, e.g., up to 3 Atm. without a traumatic extension of the vessel. Thus, at higher pressures beyond 3 Atm., the increase of the artery's volume is small, not causing serious harm to the artery, i.e., dissection or the like.

Experiments carried out on over 100 patients undergoing computerized PTCA procedure, showed that the optimal time for increasing the balloon's pressure in each cycle of the procedure was 20 sec.

A unique processor controlled procedure, especially adapted for this method, allows raising pressures dependent on time in two ways: (a) linear raise of pressure; (b) exponential raise of pressure. Pressure raised linearly is homogeneous and is carried out at a constant rate. In this manner, "soft" lesions with light calcifications are expanded gradually. Linear inflation is recommended in default inflations when an artery has already been opened and inflation data (pressure vs. volume) for the specific case is updated in the processor's memory. "Rigid" lesions, heavily calcified, are better treated when pressure is exponentially raised. The dependence of pressure on time is calculated for each 0.25 Atm. by the elasticity and/or stiffness of the plaque.

When the pressure reaches the preset level, it is maintained at this constant upper limit for a predetermined period of time, as depicted by section b of the characteristic curve. At the end of this period, the balloon is rapidly deflated, by reducing the pressure to the lowest level (e.g., creating a vacuum), at the fastest rate within the system's capability, as illustrated by line c. Following the deflation there commences a relaxation period, line d, thereby completing a cycle composed of four stages or phases a to d.

The duration of each phase of the cycle is preset by the operator as required. While in FIG. 3 the durations of the four phases of a single cycle as illustrated by the curves a, b, c, and d are shown to be substantially equal, e.g., 20 seconds each, the duration of any phase can be controlled and varied according to specific predetermined or real-time considerations. Moreover, at any time during the operation, it is possible to override the system's operation by switching the system to cause the inflator pump to evacuate the balloon or to manual operation. On the other hand, as seen in FIG. 2B, during the inflation of the balloon, and during stage b, a constant check is performed at block 28, with regard to the proper operation of the system.

Optionally, after the completion of the first cycle, the system initiates repetitions of such cycles, wherein in each additional cycle, the balloon is inflated to a pressure higher than the pressure in the previous cycle, e.g., to a pressure higher by one atmosphere. This procedure may be repeated until the maximal preset balloon pressure, e.g., 12 Atm., is attained.

Referring to FIG. 2C, while the balloon's inflation and deflation cycles are repeated, the operator checks whether or not the balloon is completely open by fluoroscopy. Should the balloon not open completely when attaining the highest preset pressure, the latter may be controllably raised and repeated until a satisfactory artery dilation is attained.

The rate of inflation of the balloon during the entire procedure can be constantly determined, based on feedback information as follows:

The generator 8 is activated by the processor and control unit 6 to generate pulses of constant width, and the transducer 2 measures the pressure applied to the balloon at each step. Every, e.g., quarter of an atmosphere, the time that it took to apply the pressure to the balloon is rechecked and recalcuated for the next quarter of an atmosphere to come. For example, at the beginning of each cycle the processor calculates the number of quarters and time necessary to reach an upper limit of a preset atmospheric pressure. The assessed time for reaching upper limit pressure is then divided by the number of segments calculated to result in homogenic time raise for each segment. Since the plaque hardness in an artery varies during inflation procedure when the balloon contacts the plaque, it might reach a certain segment more quickly or more slowly. In this case, the excessive/deficit time is subtracted/added respectively, to the remaining time needed to complete the remaining number of segments. The new time is then divided by the remaining number of segments and thus, a new time value for completing a segment is again obtained. This procedure is repeated throughout the inflation phase.

Simultaneously, the processor and control unit is updated with the number of pulses already transmitted to the step motor 10 for each of the pressure increments during phase a, as read by the pressure sensor and transducer 2 and transmitted via the converter 4 to the processor 6, so as to correct the rate of inflation in real time, to assure as much as possible the gradual inflation of the balloon.

During phase b, the pressure is kept constant and additional pressure is applied in cases where a decrease in pressure is detected due to, e.g., a change in the vessel wall's elasticity. At the end of phase c, the balloon is completely deflated, thus allowing blood to freely flow through the artery during phase d for a preset period before the commencement of the next cycle. Hence, as can be understood, the determination and monitoring of the pressure and number of pulses transmitted to the stepping motor will control in real-time the desired preset balloon inflation and deflation pressures and rates during each cycle and the number of cycles to be performed, all in accordance with the response of the artery to the balloon's performance.

At the end of the procedure, the data accumulated and stored by the processor can advantageously be graphically displayed on a screen and/or printed on the display by means 36, also allowing real time observation by the operator. The displayed curves may supply important information, e.g., plaque breakage vs. dialation.

Practically, during the relaxation period d, the graphic display means 36 illustrates a graph of the balloon's volume vs. time. Hence, the correlation between balloon and lesions can be deducted as follows:

A linear curve, parallel to the x-axis, indicates no special effect.

A linear curve, gradually ascending, indicates dilation.

A linear curve, steeply ascending, indicates atheroma breakage.

If atheromatic breakage took place during inflation in a certain cycle, then the graph will clearly display this event and the physician will consider appropriate changes to the procedure.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A fluid pressure sensing and activating control system for coronary angioplasty, said system comprising:

a balloon inflation means having an output leading to a balloon inflatable by fluid for effecting predetermined controlled change in the volume of said balloon;

a fluid conduit connector attached to the output of said balloon inflation means;

a fluid pressure sensor and transducer connected to the output of said balloon inflation means and directly contacting said fluid for measuring the actual fluid pressure applied to the balloon by said inflation means;

a processor and control unit for receiving signals from said pressure sensor and transducer via an A/D converter;

a pulse width generator for receiving signals from said processor for activating said balloon inflation means.

2. The system as claimed in claim 1, wherein said balloon inflation means comprises a stepping motor controlling a balloon inflator fluid pump.

3. The system as claimed in claim 1, further comprising display and/or data printing means, electrically connected to said processor and control unit.

4. The system as claimed in claim 1, wherein said generator is set to emit pulses of constant width and said processor and control unit controls the duration of time between emission of consecutive pulses.

5. A method for dilating a section of an elastic conduit by means of an inflatable balloon inserted therein, comprising the steps of:

a) providing a system including balloon means, balloon inflating means, pressure monitoring means, pulse width generator means, and control means;

b) gradually inflating said balloon by means of fluid to a first maximal pressure, during a preset first period of time;

c) generating pressure signals representing pressure in said balloon by means of said pressure monitoring means during inflation;

d) generating inflation signals by means of said control means and said pulse width generator means in response to said pressure signals, said inflation signals being used to control the rate of inflating said balloon during said preset first period of time;

e) retaining said first maximal pressure inside the balloon for a preset second period of time;

f) rapidly deflating said balloon to a minimal pressure;

g) retaining said minimal pressure for a predetermined period of time; and h) repeating steps (b) to (g), each time increasing the pressure of step (b) to a pressure higher than the previously inflated maximal pressure.

6. The method as claimed in claim 5, wherein in step (b) the balloon is gradually inflated so as to substantially at least partially follow an exponential pressure vs. time curve, or an exponential pressure vs. volume curve.

7. The method as claimed in claim 6, wherein said minimal pressure in step (f) is a vacuum.

8. The method as claimed in claim 5, further comprising the step of constantly monitoring the pressure inside said balloon during step (e), and determining whether there is a loss of pressure caused by a puncture or rupture of the balloon, or any by any other fluid leak in the system.

9. The method as claimed in claim 5, wherein the durations of steps (b), (e) and (g) are substantially equal.

10. The method as claimed in claim 5, wherein said pressure monitoring means comprises pressure sensing means and an analog to digital converter which produces digital signals received by said control means, said control means in turn producing digital signals which are transmitted to said pulse width generator.

* * * * *